United States Patent [19]
Mathisen et al.

[11] 3,986,778
[45] Oct. 19, 1976

[54] SPECTROPHOTOMETER SAMPLE HOLDER

[75] Inventors: Einar S. Mathisen; Alvin H. Tong, both of Poughkeepsie, N.Y.

[73] Assignee: International Business Machines Corporation, Armonk, N.Y.

[22] Filed: Oct. 1, 1975

[21] Appl. No.: 618,522

[52] U.S. Cl. .............................. 356/244; 250/227; 356/96; 356/173; 356/210
[51] Int. Cl.² ...................... G01N 21/16; G01J 3/46
[58] Field of Search ............ 356/96, 172, 173, 209, 356/210, 243, 244; 250/227; 350/81

[56] References Cited
UNITED STATES PATENTS
3,885,878   5/1975   Ishak.................................. 350/227

Primary Examiner—Vincent P. McGraw
Attorney, Agent, or Firm—Douglas R. McKechnie

[57] ABSTRACT

A spectrophotometer system is especially adapted for analyzing the colors of textiles. A sample holder includes a base that clamps a textile sample on a supporting surface. Slidably mounted on the base is a slider that is movable between two positions. In one position, an opening exposes the area to be analyzed. In the other position, a fiber optic head assembly overlies the area to be analyzed, the assembly including at least one fiber optic bundle for projecting light onto the sample and at least one other fiber optic bundle for receiving light reflected from the sample. A switch is mounted at one end of the base and is actuated when the slider is in the other position so as to provide an electrical signal indicating that a reading may be taken or analyzed by the spectrophotometer.

5 Claims, 2 Drawing Figures

SPECTROPHOTOMETER SAMPLE HOLDER

FIELD OF THE INVENTION

This invention relates to spectrophotometer sample holders and, more particularly to a sample holder for analyzing the color of textiles comprised of patterns which is difficult to locate for measurements of areas of interest.

Spectrophotometers are useful in analyzing the colors of textiles. In general, such a device includes a source of polychromatic light that is used to illuminate a small area of the textile material. Light reflected from the sample is transmitted to a detector. A monochromator is included in the light path either before or after the sample so that the light reflected from the sample can be analyzed over a range of wavelengths.

The illumination of the sample and collection of the resultant reflected light for analysis presents some difficulty. One example is that a given sample material may not be uniformly dyed to the same color so that the operator would like to either select different areas for analysis or to select a particular area for analysis. The difficulty then is to obtain accurate readings over only that area of concern.

Another problem connected with measuring the color of textile samples is to be able to obtain reproducible results. One way to aid in accomplishing this, is to illuminate the sample at right angles to it so that the angle of illumination is always constant. By locating a light collector, that is the element that receives the reflected light and transmits it towards the detector, at an angle of 45°, any specular component from a reflected material is greatly minimized so that the light analysis is done primarily upon diffuse reflected light. However, with only a single collector, it has been found that such a device is susceptible to variations due to the orientation of the textile fibers. To overcome this, a plurality of light collectors are arranged around the light illuminating element. An example of a light illuminating and collecting system of this nature is disclosed in U.S. Pat. No. 3,885,878 — Ishak which discloses a color measuring device for measuring tri-stimulus values and in which employs tri-stimulus type of filters associated with the collection elements. With light illumination and collection systems of this nature, especially where fiber optic bundles are used to illuminate the sample and to collect the collective light, the resultant assembly becomes a little cumbersome to handle and to locate over the precise area to be analyzed.

SUMMARY OF THE INVENTION

In view of the foregoing, one of the objects of the invention is to provide a spectrophotometer sample holder with a sample illumination and collection system that can be readily located over a small area for analysis of the color of that area.

Another object is to provide a reproducible sample collection and illumination system that is not affected by different textile fiber orientations.

A further object is to provide a sample illumination and collection system for a spectrophotometer with an interlock so that the readings can be taken only when the sample illumination and collection system is correctly positioned over the desired area.

Briefly stated, the invention comprises a sample holder that has a base member provided with an elongated opening, the base member being adapted to clamp or hold-down by gravity a test sample on some form of a support surface. A slider is mounted on the base member within the opening for movement between two positions. The slider has an opening exposed for view so that when in one position, an area of the sample to be analyzed is exposed. In the other position, a light illumination and collection system is positioned above the area to illuminate it with light and to collect the light reflected therefrom. In this other position, the slider actuates a miniature switch that provides an interlock or control so that a reading can be accomplished only when the switch is actuated.

Other objects, advantages and features of the invention will be apparent from the following more detailed description of a preferred embodiment of the invention as illustrated in the accompanying drawing.

THE DRAWING

FIG. 1 is a diagram of a spectrophotometer, partly schematic, partly in perspective and partly exploded, incorporating the preferred embodiment of the invention; and FIG. 2 is an elevational view, partly in section, taken along lines 2—2 of FIG. 1.

DETAILED DESCRIPTION

Figure 1:
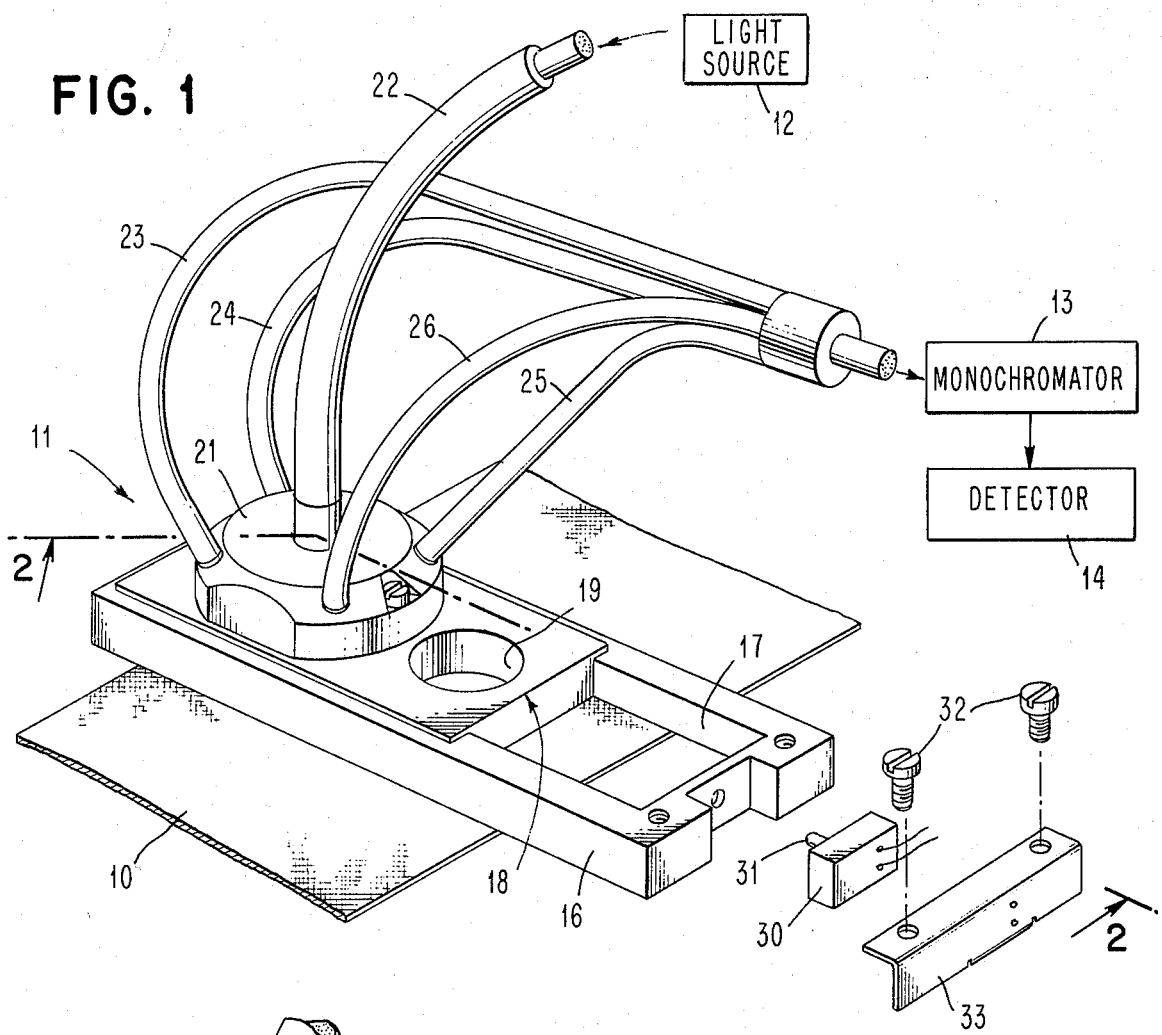

Referring now to the drawing, the invention is illustrated as being embodied in a spectrophotometer especially adapted for analyzing the color of a textile sample 10. A spectrophotometer comprises a sample holder 11, a conventional polychromatic light source 12 for illuminating the sample, a conventional monochromator 13 that converts the wide band of spectro-energy reflected from a sample 10 into narrow bandwidth so that the range of light from the sample can be analyzed, and a conventional detector 14 which receives light from the monochromator 13 and converts it to an electrical signal proportional to the intensity of the light received thereby.

It is intended that the test sample 10 be placed upon a suitable support surface such as a table. Holder 11 is of such a size that it can be readily grasped manually by an operator and placed upon sample 10 so as to hold it down or clamp it upon the surface. The sample handler would be manually manipulated until located as described below. Holder 11 comprises a rectangular annulus or base 16 provided with an elongated rectangular opening 17. A slider assembly 18 is slidably supported on base 16 and includes a first circular opening or reticle 19 and a second circular opening 20 in which is mounted a fiber optic head housing 21. A fiber optic bundle 22 of randomly oriented strands receives light from source 12 and has its lower end mounted fixedly in housing 21 whereby the axis of the lower end of the bundle is at right angles to the test sample 10 and is aligned with the center of opening 20. Four fiber optic bundles 23 - 26 of randomly oriented fiber strands have their lower ends mounted in housing 21 whereby the axis of each bundle is a 45° to the axis of bundle 22, the respective axes of the bundles intersecting with each other and with the axis of bundle 22 at the surface of sample 10. The other ends of the fiber optic bundles 23 - 26 are collected and gathered to form a single bundle of randomly oriented fibers that is connected to monochromator 13.

Figure 2:
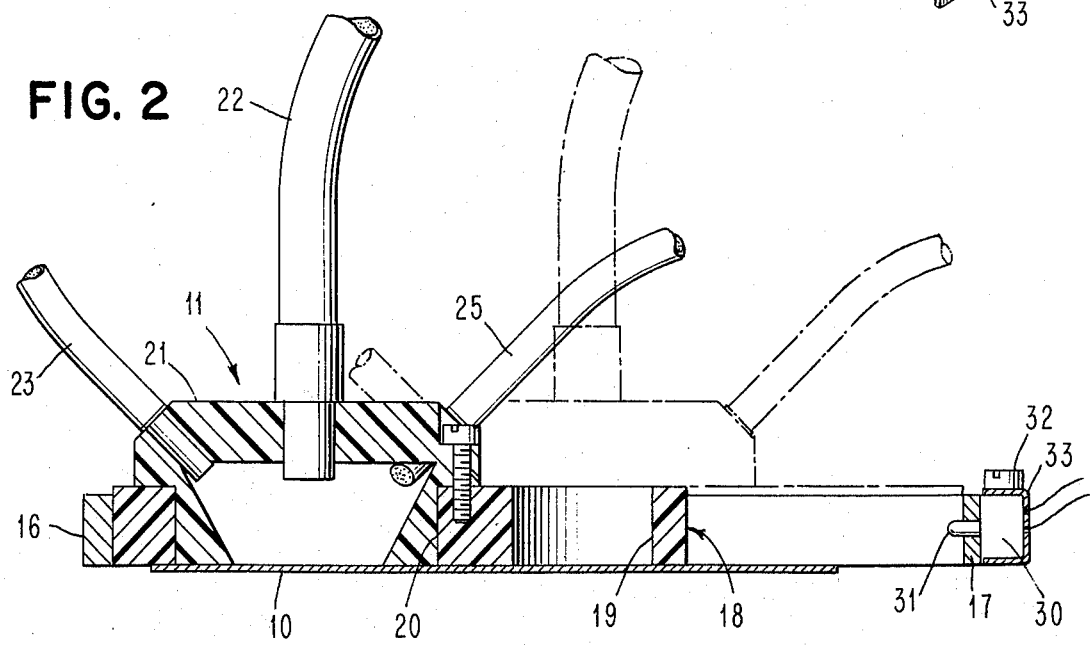

A switch assembly or switch 30, including an actuator 31, is mounted on one end of base 16 whereby the actuator extends into opening 17 for actuation of the switch when slider assembly 18 is moved against the end wall on which the switch is mounted, to the position shown in dotted lines in FIG. 2. Switch 30 is held in place by screws 32 and an end cap 33.

The length of slider 18 in opening 17 is less than the length of the opening by an amount that is substantially equal to the distance between the centers of openings 19 and 20. This allows then, the operator to place the slider assembly in one limiting position away from switch 30. The handler 11 may then be positioned over the desired area of sample 10 in which such area is exposed for view through opening 19. Then, by sliding slider 18 to the other limiting position wherein switch 30 is actuated, the lower end of bundle 22 is positioned directly over the center of the area that was initially exposed for view and which the operator selected for analysis. In such a position, the light from source 22 is used to illuminate the area of the sample beneath it. The lower walls of housing 21 abut the top of the sample. Housing 21 is formed of an opaque material to exclude any stray light. Light reflected from sample 10 is collected by the bundles 23 – 26 which directs the combined resultant light to the monochromator 13.

The actuation of switch 30 may be used to control the intensity of the light source so that it is kept in either a standby or low-level condition until the slider is correctly positioned. Then, the level of illumination can be increased. Alternatively, the level of illumination can be constant and the actuation of switch 30 used to merely provide a ready signal indicating to other circuits that a correct reading can now be obtained.

It should be apparent to those skilled in the art that various changes can be made in the details and arrangement of parts without departing from the spirit and scope of the invention as defined in the attended claims.

What is claimed is:

1. In a spectrophotometer for analyzing the color in a test sample, the combination comprising:

a base member adapted to be juxtaposed to said sample and having a first opening therein;

a slider assembly supported by said base member and being movable between two different positions, said assembly extending into said first opening and having second and third openings therein, said second opening being exposed so that an operator can observe a predetermined area of said test sample;

a fiber optic head assembly mounted in said third opening and having a first fiber optic bundle for directing light onto said test sample and a second bundle for receiving light reflected from said sample, whereby said operator can first select a predetermined area of said sample to be analyzed by aligning said second opening therewith when said slider is in said one position, and thereafter move said slider assembly to said other position whereby the fiber optic head is positioned adjacent to such area.

2. The combination of claim 1 wherein said slider assembly is movable between two limiting positions spaced apart the same distance as the centers of said second and third openings.

3. The combination of claim 2 wherein end walls of said base member define the limiting positions of movement of said slider assembly, and said combination further comprises a switch mounted on said base for actuation when said slider assembly is in a position for illuminating the area of the test sample to be analyzed.

4. The combination of claim 1 wherein said first bundle extends normal to the surface of said sample, and said second bundle extends at an angle of 45° relative to said sample, the axes of said first and second bundles intersecting at substantially the surface of said sample.

5. The combination of claim 4 comprising a plurality of additional fiber optic bundles arranged similarly to said second bundle, said additional bundles and said second bundle having common ends collected together to form a single bundle.

* * * * *